(12) United States Patent
Zhuang

(10) Patent No.: US 9,092,705 B2  
(45) Date of Patent: Jul. 28, 2015

(54) METHOD OF TELE-TRANSMITTING INFORMATION OF A MEDICAL DEVICE AND A MEDICAL DEVICE THEREOF

(71) Applicant: BMC Medical Co., Ltd., Beijing (CN)

(72) Inventor: Zhi Zhuang, Beijing (CN)

( * ) Notice: Subject to any disclaimer, the term of this patent is extended or adjusted under 35 U.S.C. 154(b) by 0 days.

(21) Appl. No.: 14/298,885

(22) Filed: Jun. 7, 2014

(65) Prior Publication Data

US 2014/0263616 A1    Sep. 18, 2014

Related U.S. Application Data

(63) Continuation of application No. PCT/CN2013/079412, filed on Jul. 15, 2013.

(51) Int. Cl.
| | |
|---|---|
| *G06K 19/00* | (2006.01) |
| *G06K 19/06* | (2006.01) |
| *G06F 19/00* | (2011.01) |
| *G06F 17/30* | (2006.01) |

(52) U.S. Cl.
CPC .......... *G06K 19/06028* (2013.01); *G06F 17/30* (2013.01); *G06F 19/3418* (2013.01)

(58) Field of Classification Search
USPC .................................. 235/375, 494
See application file for complete search history.

(56) References Cited

U.S. PATENT DOCUMENTS

2008/0149701 A1*   6/2008   Lane ............................ 235/375

FOREIGN PATENT DOCUMENTS

CN    201080010193.9    2/2012

* cited by examiner

*Primary Examiner* — Christle I Marshall  
(74) *Attorney, Agent, or Firm* — Flener IP Law; Zareefa B. Flener

(57) ABSTRACT

A method of tele-transmitting information of a medical device, a medical device thereof, a method of data reading and a data reading device are provided. By using the technical scheme of the present invention, the tele-transmission of the medical device information could be implemented without any modification of the medical device. Wherein, the method of tele-transmitting information of medical device includes: collecting and detecting therapy and/or status information of the medical device; transforming the therapy and/or status information of the medical device to one or more barcodes; outputting the one or more barcodes via an output device of the medical device.

14 Claims, 8 Drawing Sheets

METHOD OF TELE-TRANSMITTING INFORMATION OF A MEDICAL DEVICE AND A MEDICAL DEVICE THEREOF

CROSS-REFERENCE TO RELATED APPLICATION

This application is Continuation application of PCT application Serial No. PCT/CN2013/079412, filed on Jul. 15, 2013 which claims priority from CN Patent Application Serial No. 201210245802.x, filed on Jul. 16, 2012, and also claims priority from CN Patent Application Serial No. 201210245837.3, filed on Jul. 16, 2012.

FIELD OF THE INVENTION

The present invention is related to medical device technology, especially related to a method of tele-transmitting information of a medical device, a medical device thereof, a data reading device and method.

BACKGROUND OF THE INVENTION

As constant application of family therapy technology, several kinds of family medical devices were invented and marketed at present. To analyze medical information, some medical devices are required to transmit status information to hospitals or third parties periodically or at any time. Currently, the status information of a medical device is transmitted generally through an internet communication device and/or protocol; or through a removable storage device, i.e., a patient plugs a removable storage device in the medical device to store the status information, then sends the removable storage device to a hospital or third party, and further the hospital or third party returns the removable storage device to the patient after confirmation. The status information of a medical device may also be transmitted by a phone call or face-to-face oral communication between the patient and the hospital, and so on.

However, the current methods for transmitting the information of the medical device are imperfect. Adding internet communication function or removable storage interface may increase the cost of the medical device, and those added functions cannot help improving the therapy effect of the medical device, so patients may not want to pay for those functions. Transmitting the status information by a phone call or oral communication may lead to information omission, misstatement, concealing, etc., which may cause information analysis errors and even misjudgments of therapy programs, and the therapy effect may be affected consequently.

Therefore, a method of tele-transmitting information of a medical device and a medical device thereof are needed to overcome shortcomings in the prior art.

SUMMARY OF THE INVENTION

Embodiments of the present invention provides a method of tele-transmitting information of a medical device, a medical device thereof, a method for data reading and a data reading device. By using the technical scheme of the present invention, the information of the medical device information can be tele-transmitted without any modification of the medical device.

A method of tele-transmitting information of a medical device provided by an embodiment of the present invention includes:

collecting and detecting therapy and/or status information of the medical device;

transforming the therapy and/or status information of the medical device to one or more barcodes;

outputting the one or more barcodes via an output device of the medical device.

A medical device provided by an embodiment of the present invention, includes:

a detecting module, adapted to collect and detect therapy information and/or status information of the medical device;

a code transforming module, adapted to transform the therapy and/or status information of the medical device to one or more barcodes;

an output module, adapted to output the one or more barcodes generated by the code transforming module.

A method for data reading provided by an embodiment of the present invention includes:

reading one or more barcodes output by a medical device;

parsing the one or more barcodes to get therapy information and/or status information from the barcodes;

generating a report according to the therapy information and/or status information.

A data reading device provided by an embodiment of the present invention includes:

a reading module, adapted to read barcodes output by a medical device;

a parsing module, adapted to parse the one or more barcodes to get therapy information and/or status information from the barcodes;

a report generating module, adapted to generate a report based on the information read out by the parsing module.

By using the method of tele-transmitting information of a medical device, the medical device thereof, the method for data reading and the data reading device, provided by the embodiments of the present invention, the information detected and collected by the medical device is transformed to the barcodes and displayed on the output device of the medical device without any modification of the medical device. When the therapy information is required to be transmitted to a hospital or doctor, the information could be acquired easily by parsing the barcodes via an external device. In this case, the veracity of the information can be ensured and the user tampering can be avoided at the same time. In addition, by displaying the information in the form of barcodes rather than plaintext, some information which had better to uncover from the patient can be shield, which is also a reflection of the humane medical care.

DETAILED DESCRIPTION OF THE INVENTION

The embodiments of the present invention are described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be through and complete, and will fully convey the scope of the invention to those skilled in the art. Among other things, the present invention may be embodied as systems, methods or devices. The following detailed description should not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "according to an embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on". The term "coupled" implies that the elements may be directly connected together or may be coupled through one or more intervening elements. Further reference may be made to an embodiment where a component is implemented and multiple like or identical components are implemented.

While the embodiments make reference to certain events this is not intended to be a limitation of the embodiments of the present invention and such is equally applicable to any event where goods or services are offered to a consumer.

Further, the order of the steps in the present embodiment is exemplary and is not intended to be a limitation on the embodiments of the present invention. It is contemplated that the present invention includes the process being practiced in other orders and/or with intermediary steps and/or processes.

Figure 1:
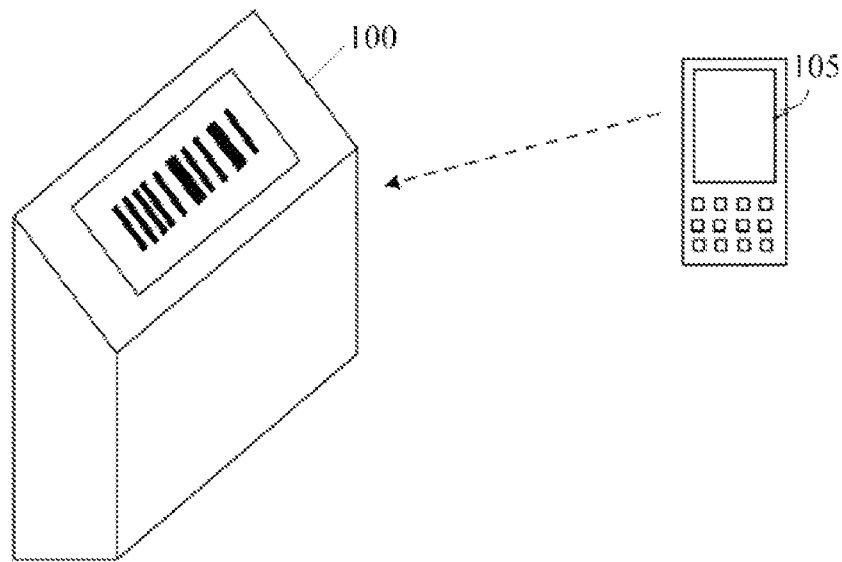
FIG. 1 illustrates the structure diagram of a system of tele-transmitting information of a medical device according to an embodiment of the present invention.

FIG. 1 illustrates a system of tele-transmitting-information of a medical device according to an embodiment of the present invention. As shown in FIG. 1, the system includes:

A medical device 100, has a specific curing function, and further collects variety of therapy information and/or status information while it is being used; and transforms the collected therapy information and/or status information to barcodes, and output the barcodes. A data reading device 105 is adapted to scan the barcodes output by the medical device 100, and to generate a therapy report according to the information obtained from parsing the scanned barcodes and send the therapy report generated to a medical institution or third party.

For simplification, the barcode shown in FIG. 1 is a simple one-dimensional code. Those skilled in the art can understand that, practically, the forms of the barcode may be varied. According to an embodiment of the present invention, the barcode is preferably an international standardization barcode, such as a string code (for example an ASCII code or other string codes in other coding ways), a one-dimensional code, two-dimensional code, three-dimensional code or complex code. As an example, the one-dimensional code may be a JAN code, an ITF code, a NW-7 code, etc. The two-dimensional code may be a QR (Quick Response) code, a PDF417 code, etc. The three-dimensional code may be the barcode developed by the Japanese company "Content Idea of Asia". The complex code is a kind of code combined by the codes mentioned above.

According to an embodiment of the present invention, a data reading device may be an existing mobile terminal or electronic device with barcode reading function. At this situation, the data reading device may also share other functions with the existing devices, such as cameras, Bluetooth, wifi, etc. In this way, the medical report generated could be provided to the medical institution and third party by the data reading device in various ways.

According to an embodiment of the present invention, the therapy information read out by the data reading device 105 may be in form of a string code (will be described specifically in following embodiments), in this case, the system may further include a string code parsing system, which could be installed on a user side, or on a server side in the manner of web service. I.e., the user may input or send the string code to a local software/system (the string code parsing system) installed on the user side to obtain the plaintext of the therapy information and/or status information; or the user may send the string code to a web site (the string code parsing system is installed on the server side) to obtain the plaintext of the therapy information and/or status information. In this situation, the therapy report may be generated directly by the string code parsing system.

By using the system provided by the embodiment of the present invention, no complex modification of the existing medical device is required. Instead of adding a new communication module in the existing medical device, the therapy information and/or status information is transformed to the barcodes so that those information could be obtained and transmitted to the medical institution by the data reading device later. Since the data reading device could be integrated with an existing mobile terminal or electronic device, the information transmitting function of the medical device could be further extended via communication modules of the existing mobile terminal or electronic device. In this way, the medical device without a communication module could also be used by integrating with an external device with a communication module. Moreover, through the barcodes, during the process of transmitting the therapy and/or status information to the hospital, the plaintext of the therapy and/or status information could be concealed from the user or patient; and the user or patient is still able to determine which information would be sent to the medical institution and third party (by pointing out the specified barcodes to be scanned).

Figure 2:
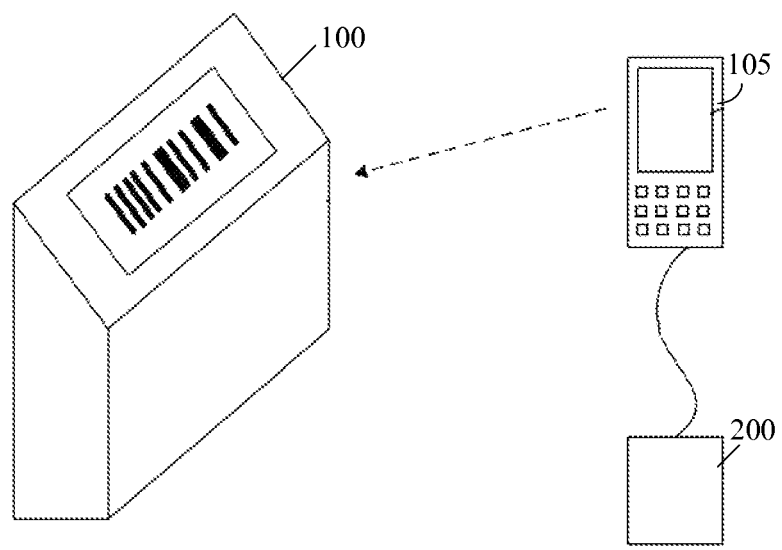
FIG. 2 illustrates the structure diagram of a system of tele-transmitting information of a medical device according to another embodiment of the present invention.

FIG. 2 illustrates the structure of a system of tele-transmitting information of a medical device according to another embodiment of the present invention. As shown in FIG. 2, compared with the system shown in FIG. 1, the system further includes a data parsing/display device 200 which is on the side of the medical device or a third party. In this case, the data reading device 105 will not generate a therapy report directly but transform the barcodes to transmittable data, and then the transmittable data is transmitted to the data parsing/display device 200 through the transmission function of the data reading device. The data parsing/display device 200 analyses the transmittable data to obtain the barcodes, parses the barcodes to obtain the therapy and/or status information and then displays the obtained therapy and/or status information, as a reference for doctors. According to an embodiment of the present invention, when the barcodes are string codes, the data parsing/display device 200 may be the same with or have the same functions with the string code parsing system shown in FIG. 1.

Those skilled in the art can also understand that, although only one-dimensional barcode is shown in FIG. 1 as an example, the barcodes may be in a variety of forms practically.

According to an embodiment of the present invention, the data parsing/display device may be a PC terminal, cell phone, tablet or other hand-held terminals as long as they support data reception function, parsing function, as well as display function.

Figure 3:
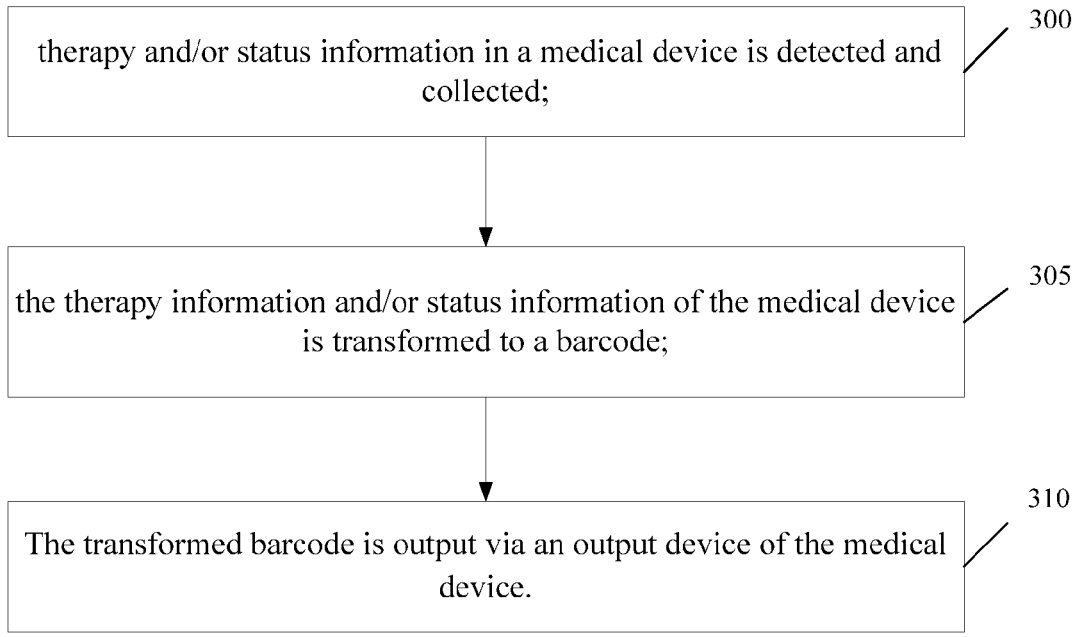
FIG. 3 illustrates the flow diagram of a method of tele-transmitting information of medical a device according to an embodiment of the present invention.

FIG. 3 is the flow diagram of a method of tele-transmitting information of a medical device according to an embodiment of the present invention. As shown in FIG. 3, The method includes following steps.

Step 300: therapy and/or status information in the medical device is detected and collected.

Depending on functions of the medical device or the illness of a patient (which may be treated differently by a doctor), the therapy and/or status information to be detected and collected may be slightly different. According to an embodiment of the present invention, a user interface may be provided to enable users to select from all kinds of therapy and/or status information which can be detected by the current medical device. The "All selected" mode is in default.

For example, when the medical device is a ventilation therapy device, the status information may include: the number of treatment day, average daily treatment time and/or treatment pressure (average pressure P95 or P90). In an example, AHI (Apnea Hypopneas Index), snoring index and/or air leakage may also be included.

According to an embodiment of the present invention, the therapy and/or status information may be detected by a sensor of the medical device. For example, the air pressure and air flow provided by the ventilation therapy device may be detected by a pressure sensor and a flow sensor separately, or the user's snore may be detected by a sound sensor.

In an embodiment, the therapy and/or status information may be detected by an additional sensor beyond the medical device.

The status information includes at least one kind of: treatment day, average daily treatment time, treatment pressure, AHI, snoring index and air leakage.

Since a hospital or medical institution may receive information of several users at the same time, according to an embodiment of the present invention, in order to distinguish the received status information of different users, the status information may further include identity information of the medical device and/or that of the user.

Herein, the identity information of the medical device may be the model information, not necessarily the unique indicated information of the medical device. The identity information of the user may be the information input manually by the user, which may be a unique indicated kind or not. Certainly, if the identity information of the medical device is unique, the identity information of the user is not necessary then.

Step 305: the therapy and/or status information of the medical device is transformed to a barcode or barcodes.

The barcode may preferably be an international standardization barcode, such as a string code (e.g. an ASCII code), a one-dimensional code, two-dimensional code, three-dimensional code or complex code. As an example, the one-dimensional code may be a JAN code, an ITF code, a NW-7 code, etc. The two-dimensional code may be a QR (Quick Response) code, a PDF417 code, etc. The three-dimensional code may be a barcode developed by a Japanese company named as "Content Idea of Asia". According to an embodiment of the present invention, the complex code is a kind of code combined by the above codes. According to an embodiment of the present invention, the string code may be in the form of character strings.

Since different barcodes may carry different amount of information, so the form of the barcode is determined by the requirement of the amount of information. For example, for a medical device with a few functions, the status information may be transformed to one-dimensional barcodes; for a medical device with multiple functions, the status information may be transformed to string codes, two-dimensional codes, three-dimensional codes or complex codes. Naturally, the amount of information to be transformed is another criterion to determine the form of barcodes.

According to an embodiment of the present invention, the therapy and/or status information may be transformed to a data frame firstly, and then the data frame is transformed to the barcode.

The following table indicates an example of a data frame formed by the therapy and/or status information. As shown, the data frame includes a frame header, information body, check code and frame tail. Herein, the frame header and the frame tail may be specified, the check code may employ a checksum verification method or a CRC verification method to verify the integrity of the frame. Those skilled in the art can understand that, the following table is just an example.

| 1 byte | ○ ○ ○ ○ ○ | 1 byte | 1 byte |
|---|---|---|---|
| Frame header 0xA5 | Information 0x77, 0x77, 0x77 (the ASCII value of each character) | Check code Check | Frame tail 0x55 |

The data frame shown in the above table may be transformed to a two-dimensional code thereafter.

Step 310: the barcode(s) are output via an output device of the medical device.

According to an embodiment of the present invention, if the output device of the medical device is a small printer port, the transformed barcodes may be printed out on papers; then the papers with barcodes are transmitted to the hospital or health institution, or, the printed barcodes are read by a data reading device as described below and then the obtained information is sent to the hospital or health institution.

According to an embodiment of the present invention, if the output device of the medical device is a display screen, the transformed barcodes may be displayed on the screen; then the displayed barcodes are read by the data reading device as described below and then the obtained information is sent to the hospital or health institution.

According to an embodiment of the present invention, if the output device of the medical device is a kind of electron port, such as an USB port, the transformed barcodes may be output to an external storage as a U disk; then the external storage recorded the barcodes is transmitted to the hospital or health institution.

According to an embodiment of the present invention, the therapy and/or status information of a certain therapy period collected and detected may be stored in the medical device firstly, and then are transformed to the barcodes. The transformed barcodes may be stored in the medical device as well for future use. In addition, some additional information may also be pre-stored in the medical device, such as status information of the user, the status information of the medical device, the name of the measure program, the management information and so on, so as to be used in barcode transforming processes.

According to another embodiment of the present invention, when there is a need to detect total usage time (number of days from the first day using the device by the patient to the day of data reception by the hospital) and average daily usage time of the medical device, the usage time information may also be recorded, and then be transformed to the barcodes together with the other status information collected and detected in the same therapy period.

According to an embodiment of the present invention, the collected and detected status information should be statistically analyzed to estimate the therapy effect, and further to help the determination whether the therapy parameter should be adjusted. The statistical analysis result is then transformed to barcodes and sent to the hospital or health institution. Certainly, the result may also be provided to the user directly.

Figure 4:
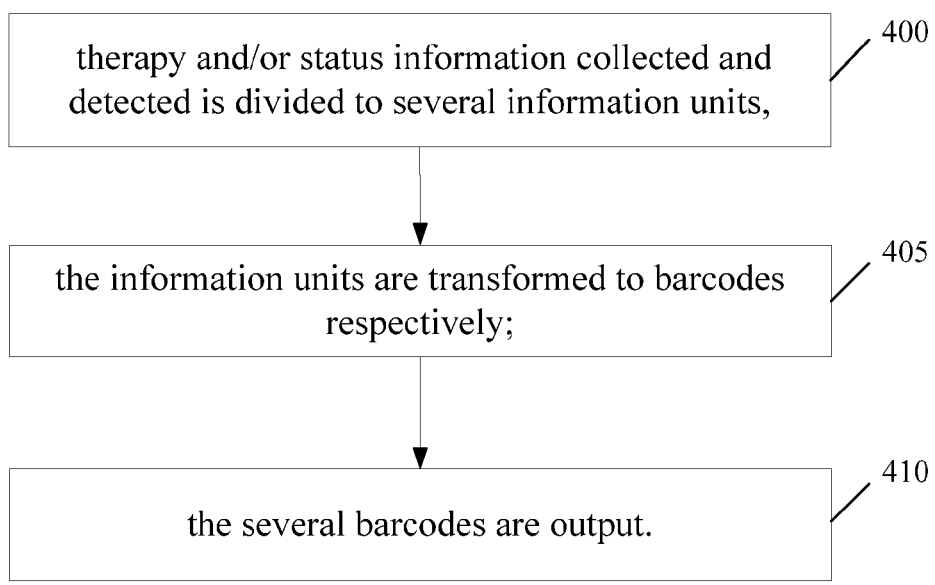
FIG. 4 illustrates the flow diagram of a method of tele-transmitting information of a medical device according to an embodiment of the present invention.

FIG. 4 is the flow diagram of a method of tele-transmitting information of a medical device according to an embodiment of the present invention. As shown in FIG. 4, the method includes following steps.

Step 400: therapy and/or status information collected and detected is divided to several information units, which will be transformed to barcodes separately. The barcodes may be one or more kinds of barcodes, as illustrated in the above embodiments.

The step may adopt the same method of Step 305 illustrated in the embodiment shown in FIG. 3.

Step 405: the information units are transformed to the barcodes respectively.

In this case, every barcode may further contain controlling data as data identification, location identification, totality identification and/or time identification, etc.

Herein, the data identification is to identify the "file" of the information unit represented in the current barcode, which is applied to determine which barcodes belong to the same "file". The said "file" means "a complete therapy and/or status information".

The location identification is to identify the location or sequence of the information unit in the current "file".

The totality identification is to identify the total number of the information units in the "file" of the current barcode.

It can determine whether all barcodes of a "file" have been read according to the number of the barcodes which have been read and the totality identification.

The time identification is to identify the output time of the current barcode and the left time required for outputting the left barcodes, to provide a reference for the user.

Those skilled in the art can understand that, the barcodes may only include part of the controlling data described above, for example, a totality identification may not be necessary in some cases, while in other cases, the time identification may be not needed, or, both of them are excluded.

Step 410: the several barcodes are output. The step may adopt the same method of Step 310 illustrated in the embodiment shown in FIG. 3.

According to an embodiment of the present invention, if the barcodes are output on a display screen, it could be set that outputting all of the barcodes at one time or outputting one barcode each time successively.

By using the method of tele-transmitting information of medical device, therapy information could be transmitted by being divided and transformed to multiple barcodes, which will satisfy the requirement of large amount of transmitted information. Besides, in some cases, comparing with transforming the large amount of information to one barcode, due to the limit performance of the two-dimensional code generation module and/or data scanning module, it is preferable to divide data into information units firstly and then transform those information units to the barcodes, which can achieve better performance and faster process speed, and may be used to improve the performance of some medical devices with poor processing capability.

According to an embodiment of the present invention, several information units may also be transformed to one barcode.

Figure 5:
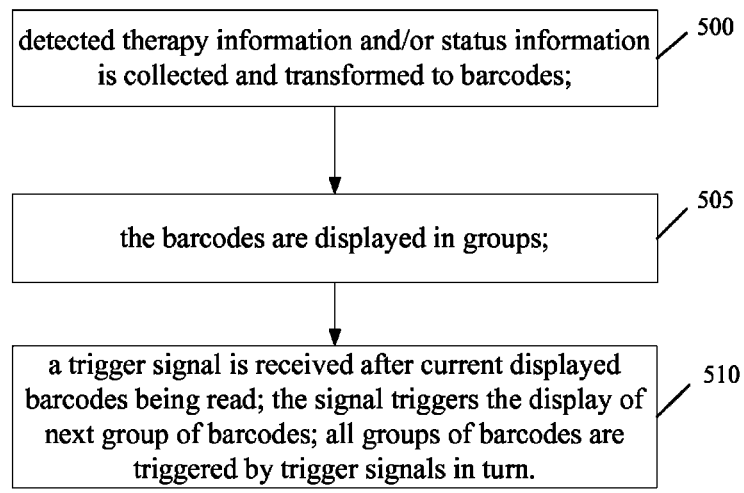
FIG. 5 illustrates the flow diagram of a method of tele-transmitting information of a medical device according to an embodiment of the present invention.

FIG. 5 is the flow diagram of a method of tele-transmitting information of medical device according to an embodiment of the present invention. As shown in FIG. 5, the method includes following steps.

Step 500: detected therapy and/or status information is collected and transformed to barcodes.

Those skilled in the art can understand that, the therapy and/or status information may be transformed in the way described in Step 305 shown in FIG. 3 or Step 400 and Step 405 shown in FIG. 4.

Step 505: the barcodes are divided and displayed in groups.

When the amount of information is too huge for the display device, the barcodes may be divided and successively displayed in groups.

According to an embodiment of the present invention, the barcodes may be equally grouped or not, as long as at least one barcode is included in each group and displayed. In some extreme cases, only one barcode is included in one group, or all barcodes belong to one group.

Step 510: a trigger signal is received after the current displayed group of barcodes being read. Herein, the trigger signal is a signal generated during or after the current displayed group of barcodes being read. The trigger signal triggers the display of a next group of barcodes; all groups of barcodes are triggered by trigger signals in turn.

According to an embodiment of the present invention, the displayed barcodes may be read via a data reading device (which will be described in detail in following embodiments) and then be transmitted to a health institution or third party. Once the trigger signal, which represents that the current group of the barcodes has been shot or scanned, is captured, the next group of barcodes will be triggered to be displayed; the process will repeat until all groups of the barcodes being shoot or scanned. This means, the number of shoot/scan times is equal to the number of the barcode groups. The display of the barcodes will stop automatically when all the barcodes have been displayed.

The trigger signal may be a signal automatically generated while the barcodes are shot or scanned by the data reading device, such as an optical and/or sound signal. For example, the trigger signal may be an optical signal generated by flashlight of the data reading device and/or a sound signal generated by a loudspeaker, or a laser signal generated during the scanning process, etc.

According to an embodiment of the present invention, the trigger signal may also be a signal generated after each group of the barcodes having been successfully shoot or scanned, e.g. a signal generated after each group of barcodes being successfully read by the data reading device, in order to make sure that the next group of barcodes is displayed after the previous barcodes have been read. Of course, the trigger signal may be generated before, during, or after the barcodes being read. Those skilled in the art can understand that, the optical or sound signal should be distinct from normal light and sound from the surroundings, The optical or sound signal could be distinguished by controlling the intensity, the type (e.g. the optical pulse signal, the sine wave optical signal and so on), the duration of the signal, etc.

The trigger signal may also be any signal artificially preset, such as a signal automatically generated by artificially presetting after shooting/scanning. Certainly, the trigger signal may also be generated manually, e.g. be generated by a patient's pressing operation.

By using the scheme of the present invention, the next group of barcodes may be displayed automatically/manually according to the trigger signal, which generated during or after previous group of barcodes being shot or scanned. As a result, work efficiency may be improved and manual operation mistakes may be avoided at the same time.

Those skilled in the art can understand that, in practical operation process, the method of transmitting the information of the medical device may be combined. All the combined methods that are able to be implemented (including any combination with existing techniques) should be considered to be within the protective scope of the present invention.

The method of tele-transmitting information of the medical device provided by the embodiment of the present invention could be implemented by hardware, software, or their combination. If by software, the method may be achieved by updating the software in a control center of the current medical device. In this case, collected and detected information may be remotely transmitted to the health institution without any modification of the control center of the current medical device (no communication devices or external devices need be added); consequently, the veracity of the information can be ensured and the information falsification can be avoided. Moreover, since the information is output via the barcodes, the patient or user cannot understand the therapy information directly, which make the medical process humane.

In the above embodiments of the present invention, the interaction among several barcodes cannot be avoided either in the process of transforming the information units to the barcodes as described in Step 405 or in the process of grouping the barcodes as described in Step 505. According to an embodiment of the present invention, check information is added into each barcode. According to another embodiment of the present invention, the information of the total number of the whole group/batch of barcodes and the serial number of the current barcode is added into each barcode, so that the barcodes may be scanned without considering the order of the barcodes, the barcodes may be scanned continuously or not, for example, the scan may start from any barcode or even discretely. Once all of the barcodes in one group have been scanned, users will be informed that the scan of the barcodes in the current group is completed. At the same time, the serial number provided could prevent that the scanning restarts from the first barcode again when there are errors in reading some barcodes. In this case, to ensure the accuracy and consistency of information, a memory may be adapted to temporarily store the generated barcodes. If there is an error in reading any barcode, the corresponding barcode is read out directly from the memory according to the serial number recognized. According to an embodiment of the present invention, the scanned and unscanned barcodes are specified respectively to avoid missing or repeat scanning.

According to an embodiment of the present invention, users may switch to scan the next barcodes by manually operating the medical device, or by using the scheme provided in the embodiment of FIG. 5. Or, the display of the next barcodes to be scanned may also be controlled at the side of a scanner (such as the reading device) automatically or by buttons. The methods of switching to scan the next barcodes at the side of the medical device or scanner are classified as four types, as shown in a following table.

| Serial No. Of Switching method | Scanner | Medical Device |
| --- | --- | --- |
| 1 | Manually | Manually |
| 2 | Manually | Automatically |
| 3 | Automatically | Manually |
| 4 | Automatically | Automatically |

Herein, the switching methods at the scanner sider are shown as follows:

| | |
| --- | --- |
| Automatically | After successfully scan and store the information, automatically switch to a scanning interface and start to scan the next barcodes |
| Manually | After successfully scan, pop up a dialog box to inform the user the successful scan, start to scan the next barcodes only after the user confirms |

Herein, the switching methods at the medical device side are shown as follows:

| | |
| --- | --- |
| Automatically | switch to display the next barcodes by monitoring an external signal (such as a flash light of a client; a prompt tone from the client) |
| Manually | switch to display the next barcodes by pressing a button of the medical device physically |

Figure 6:
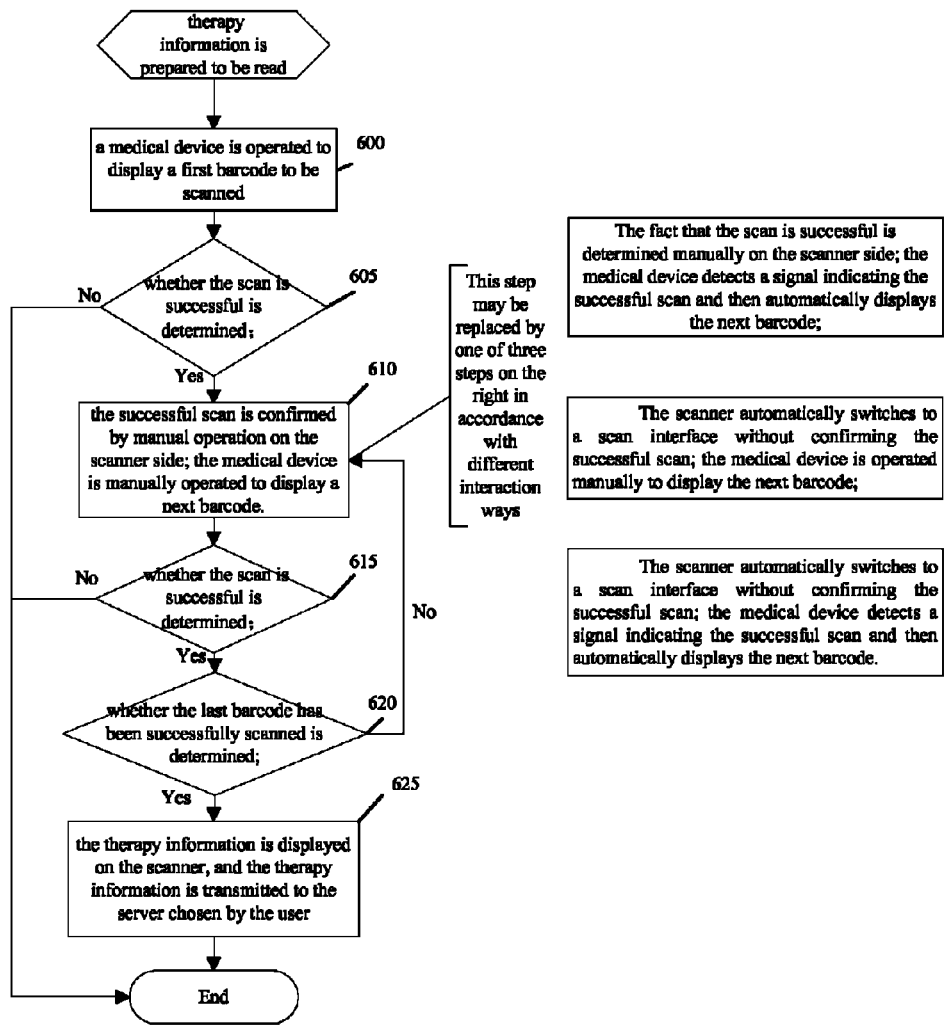
FIG. 6 illustrates the flow diagram of a method of scanning multiple barcodes according to an embodiment of the present invention.

FIG. 6 is the flow diagram of a method of tele-transmitting information of a medical device according to an embodiment of the present invention. As shown in FIG. 6, the method includes following steps.

Step 600: a scanner is opened, and a medical device is operated to display a first barcode to be scanned;

Step 605: whether the scan is successful is determined; if the scan is successful, turn to Step 610; otherwise, the procedure is terminated.

Step 610: the successful scan is confirmed by manual operation on the scanner side; the medical device is manually operated to display a next barcode.

Those skilled in the art can understand that, depending on different interaction methods of the scanner and the medical device, Step 610 may be replaced as follows:

The fact that the scan is successful is determined manually on the scanner side; the medical device detects a signal indicating the successful scan and then automatically displays the next barcode;

The scanner automatically switches to a scanning interface without confirming the successful scan; the medical device is operated manually to display the next barcode;

The scanner automatically switches to a scanning interface without confirming the successful scan; the medical device detects a signal indicating the successful scan and then automatically displays the next barcode.

Step 615: whether the scan is successful is determined; if the scan is successful, turn to Step 620; otherwise, terminate the procedure.

Step 620: whether the last barcode has been successfully scanned is determined; if yes, turn to Step 625; otherwise, return to Step 610.

Step 625: the therapy information is displayed on the scanner, and the therapy information is transmitted to a server chosen by the user, and the procedure is terminated.

Figure 7:
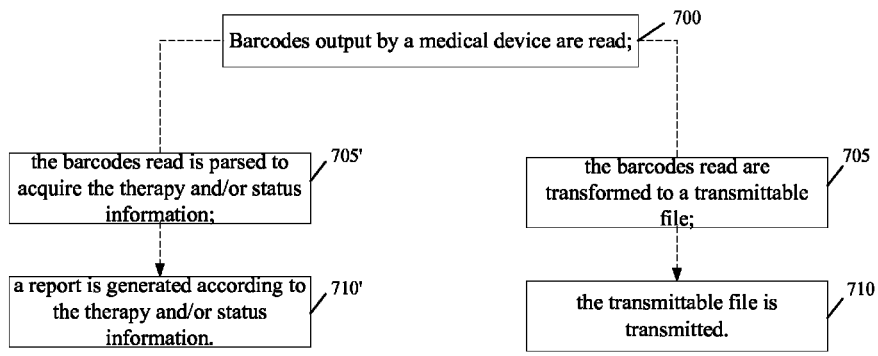
FIG. 7 illustrates the flow diagram of a method of tele-transmitting information of a medical device according to an embodiment of the present invention.

FIG. 7 is the flow diagram of a method of tele-transmitting information of a medical device according to an embodiment of the present invention. The method is applied to a data processing device. As shown in FIG. 7, the method includes following steps.

Step 700: barcodes output by a medical device are read.

As an example, the barcodes could be read by a barcode scanning device such as a scanner. According to an embodiment of the present invention, the barcodes may also be read by a photograph device. The photograph device may be any device or terminal with a camera, such as cell phones, laptops, pads, etc.

Figure 8:
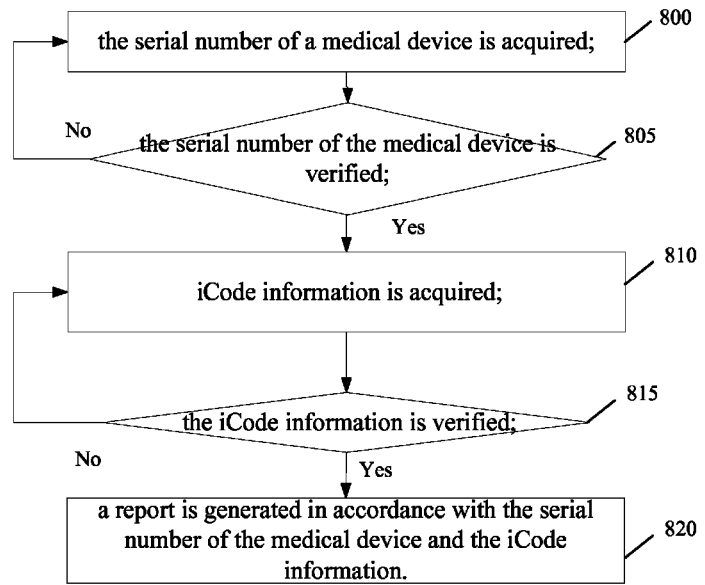
FIG. 8 illustrates the flow diagram of a method of tele-transmitting information of a medical device according to an embodiment of the present invention.

Those skilled in the art can understand that, in Step 700, an information verification method described in FIG. 8 may be used (to verify whether the therapy and/or status information match the serial number of the device).

Step 705: the barcodes read are transformed to a transmittable file. The transmittable file may be original information or advanced barcode. The original information may be the information, the data form of which is the same with that of original status information. The level of the advanced barcode is superior to the barcodes read, which makes it carry larger amount of information, so that all of information can be carried in one advanced barcode to be transmitted to a hospital or third party in one time. As an example, multiple string codes could be transformed to one two-dimensional code, one three-dimensional code or one complex barcode; several two-dimensional codes could be transformed to one three-dimensional code or one complex barcode etc.

Step 710: the transmittable file is transmitted. The file could be transmitted to the remote hospital or third party via internet, mobile communication network and other communication networks.

According to an embodiment of the present invention, the information of the medical device may be transmitted via a PC, a cell phone, etc.

In this above case, a device with data parsing and analysis function is required in the hospital or third party.

According to an embodiment of the present invention, Step 705 and Step 710 may also be replaced by Step 705' and Step 710'.

Step 705': the barcodes read is parsed to acquire the therapy and/or status information.

Step 710': a report is generated according to the therapy and/or status information.

According to an embodiment of the present invention, before/after parsing the barcodes read to acquire the therapy and/or status information, the method further includes verifying the barcodes read. If the barcodes are generated by transforming therapy and/or status information to a data frame according to a certain rule, the barcodes may be verified by: parsing the barcodes to acquire the data frame, and verifying information body of the data frame acquired according to the check code of the data frame.

FIG. 8 is the flow diagram of a method of tele-transmitting information of a medical device according to an embodiment of the present invention. The method is mainly applied to a data reading device to read a barcode output in the above embodiments. In an embodiment, when the barcode is a string code, the therapy and status information is transformed to a group of string codes in accordance with a predefined rule. Taken a respirator as an example, the therapy information may be therapy time, AHI, SNI, air leakage, adaptability, P95, etc., and the status information may be settings of therapy pressure, etc. To facilitate the description, take "iCodes" to represent the kind of barcodes in following embodiments. As shown in FIG. 8, the method includes following steps.

Step 800: a serial number of a medical device is acquired.

According to an embodiment of the present invention, the serial number may be photographed and transmitted as an image. An existing image showing the serial number may also be used. In this case, OCR image recognition technology is required to extract the serial number, so that the manual operation by a user is avoided and the process becomes user friendly.

According to an embodiment of the present invention, a manual input interface may be provided for the user to input the serial number manually.

If it fails to extract the serial number, an error message may be shown to ask the user to repeat the input; and continue to execute the next step after the serial number is extracted successfully.

Step 805: the serial number of the medical device is verified.

In one embodiment of the present invention, verifying the serial number of the medial device includes verifying whether the serial number is correct, whether characters contained in the serial number is legal, and/or whether the serial number matches serial numbers pre-stored in the system. If the verification fails, return back to Step 800; otherwise, continue with the next step.

Step 810: the iCode information of the medical device is acquired.

According to an embodiment of the present invention, as illustrated in Step 800, a photographed image or an existing image may be used, or a manual input interface may be provided.

If the acquiring fails, an error message may be shown to require the user to repeat the input, otherwise, continue with the next step.

Step 815: the iCode information is verified.

The verification of the iCode includes verifying whether its length is correct, whether the characters contained are legitimate, and/or whether the iCode matches the serial number of the medical device. If the verification fails, turn to Step 805; otherwise, continue with the next step.

Herein, if whole therapy information is consisted by n groups of iCode, after the current group of iCode is verified successfully, return to Step 805 to add a next group of iCode which matches the serial number. After all n groups of iCode have been added, continue with the next step.

Step 820: a report is generated in accordance with the serial number of the medical device and the iCode information.

According to an embodiment of the present invention, a user may choose to generate a web report to be accessed by a web browser or a local report which can be accessed by software.

If the web report is chosen, the serial number of the medical device and the correspondent iCode information acquired are transmitted to a server, and the web report is generated by the server after a successful verification of the information received. Then, the web report may be able to be downloaded by users (patients or doctors in medical institutions).

According to an embodiment of the present invention, before being transmitted, the serial number of the medical device and the correspondent iCode information are encrypted by a symmetric key or a public/private key. In this case, the server decrypts the information received firstly, and then verifies the legitimate of the information.

If the local report is chosen, it may be generated directly in accordance with the serial numbers of the medical device and the iCode information acquired.

A CRC verification is adapted for both kinds of reports.

According to the embodiment of the present invention, the report may be sent to the user directly after generation, or sent to a certain email address to facilitate the storage.

Those skilled in the art can understand that, in some embodiments, Step 800 and Step 805 may be implemented after Step 810 and Step 815, which do not affect the implementation of the present invention.

In the above embodiments, the merits of verifying the iCode include:

By verifying the correctness of the iCode information, the influence of user's disoperation and image misrecognition could be eliminated; herein, if the verification fails, a message is shown to ask the user to resubmit the information;

By verifying whether the serial number of the medical device matches the iCodes, i.e., verifying whether the iCodes are generated by the medical devices via which the iCodes are input, the report could be generated correctly; or, without a successful verification, a report with errors may be generated by directly parsing the iCodes. According to an embodiment of the present invention, at a certain time, only one group of iCode can be correctly generated by the medical device. Since the serial numbers and iCode are corresponded, if the serial number input by users is wrong, all iCodes must be wrong; if the input serial number is correct, the iCodes also would be considered as false even though only one character contained is not correct;

It can prevent any purposely tampering with the iCodes. It is very important since the iCodes may contain some reimbursement information of the user.

In an embodiment, if the serial number of the medical device and the iCodes have been transformed to a two-dimensional code at the medical device side, the serial number of the medical device and the iCodes could be acquired by scanning the two-dimensional code; and then Step 805 and Step 810 may be implemented to verify the serial number and the iCodes.

According to an embodiment of the present invention, an iCode is generated according to therapy and/or status information, and then a two-dimensional code may be generated in accordance with the iCode. The detailed process is as follows: transforming the therapy and/or status information to the iCode according to a predefined rule; decoding the iCode in accordance with the opponent rule; then determining whether the information decoded from the iCode matches the original iCode; transforming the iCode to the two-dimensional code and displaying the two-dimensional code if matches; otherwise, sending an error message to the user, indicating that it fails to generate the two-dimensional code. In an embodiment, after the therapy and/or status information is transformed to the iCode, the iCode may be directly transformed to the two-dimensional code to be displayed.

According to an embodiment of the present invention, the two-dimensional code may be generated from a number of iCodes, or from the therapy and/or status information directly.

An example is taken below to describe the process of generating an iCode and a two-dimensional code.

Suppose a number of iCodes have been generated according to therapy information/status information, the detailed iCodes and a serial number are shown as follows; meanwhile, suppose the iCodes and the serial number have been verified successfully:

The serial number of a medical device: 1208D589 iCode 1: UM6R2KGHC0802K3Q iCode 7: QX7088 GHD0G01G2N iCode 30: WN7Q7UGHB0F01F2F iCode 90: P09L7UGHB6F01F2F iCode 182: VLCG7UGHB0F01F2F iCode 365: VCJ77UGHB0F01F2F The above iCodes record the therapy and/or status information of the medical device after 1, 7, 30, 90, 182 and 365 days of treatment respectively, those ASCII codes of the iCodes represent detailed status information of those day treatment respectively.

Then, a two-dimensional code (not shown in the specification) is generated after combining the iCodes to a data frame; when the two-dimensional code is scanned, the frame is shown as follows. Herein, the frame includes a frame head "Y", a frame tail "U" and a check bit "{" besides the iCodes. Of course, a rule of generating the data frame corresponding to the two-dimensional code may be self-defined and is not limited as shown in the following table.

---

Y"SN":"1208D589","icode1":
"UM6R2KGHC0802K3Q",
"icode7":
"QX7088GHD0G01G2N",
"icode30":
"WN7Q7UGHB0F01F2F",
"icode90":
"P09L7UGHB6F01F2F",
"icode182":
"VLCG7UGHB0F01F2F",
"icode365":
"VCJ77UGHB0F01F2F"{U

---

Once the information of the above iCodes is acquired, the therapy information may be acquired by a user or doctor via an iCode decoding software installed on a mobile terminal or a web terminal. For example, in the following table, the therapy information decoded from the above iCodes is shown.

|  | Last 365 Days | Last 182 Days | Last 90 Days | Last 30 Days | Last 7 Days | Last 1 Day |
|---|---|---|---|---|---|---|
| Day Count | 365 | 182 | 90 | 30 | 7 | 1 |
| Days of Therapy (>4 h) | 2 | 2 | 2 | 2 | 1 | 0 |
| Days of Therapy (%) | 0% | 1% | 2% | 6% | 14% | 0% |
| Avg. Daily Compliance (hh:mm) | 4:02 | 4:02 | 4:02 | 4:02 | 4:16 | 1:15 |
| Average P95 (cmH2O) | 13 | 13 | 13 | 13 | 14.5 | 10 |
| Avg. Mean Pressure (cmH2O) | 9.5 | 9.5 | 9.5 | 9.5 | 10.5 | 10 |
| Avg. AHI | 19.5 | 19.5 | 19.5 | 19.5 | 20 | 37.5 |
| Avg. SNI | 35 | 35 | 35 | 35 | 38.5 | 55.5 |
| High Leak (>90 LPM) Time (%) | 0% | 0% | 0% | 0% | 0% | 0% |
| Best 30-Day Adherence Score | — | — | 20%(6:30) | — | — | — |
| iCode String | VCJ77UGH B0F01F2F | VFLCG7UGH B0F01F2F | P09L7UGH B6F01F2F | WN7Q7UGH B0F01F2F | QX7088GH D0G01G2N | UM8R2KGH C0802K3Q |

According to an embodiment of the present invention, the therapy and/or status information may be transformed to a data frame directly, then a two-dimensional code (not shown in this specification) may be generated from the data frame; when the two-dimensional code is scanned, the information after 90 days of treatment get from paring the two-dimensional code is as follows:

```
¥"SN":"1208D589",
"iCode90":"90","Days":"2",
"Comp":"4:02","P95":"13",
"MeanP":"9.5","AHI":"19.5",
"SNI":"35"òU
```

Figure 9:
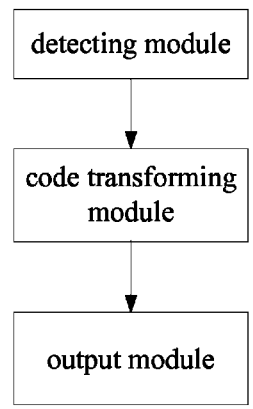
FIG. 9 illustrates the structure diagram of a medical device according to an embodiment of the present invention.

FIG. 9 illustrates the structure diagram of a medical device according to an embodiment of the present invention. As shown in FIG. 9, the medical device comprises a detecting module, a code transforming module and an output module.

The detecting module is adapted to collect and detect status information of the medical device.

The code transforming module is adapted to transform the status information, detected by the detecting module, to a barcode or barcodes.

The output module is adapted to output the barcodes generated by the code transforming module. In an embodiment, the output module may be a display device, a printer or other output devices.

Figure 10:
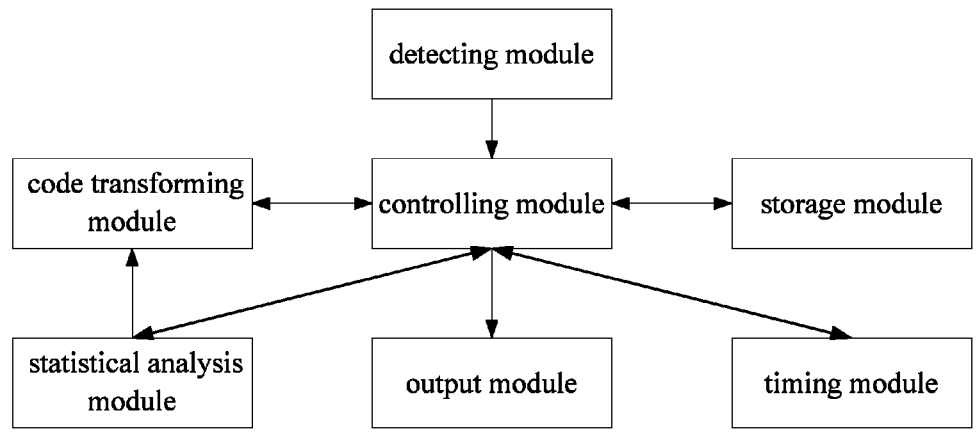
FIG. 10 illustrates the structure diagram of a medical device according to another embodiment of the present invention.

FIG. 10 illustrates the structure diagram of a medical device according to another embodiment of the present invention. As shown in FIG. 10, based on the structure shown in FIG. 9, the medical device further includes a controlling module, a storage module, a timing module, and a statistical analysis module.

The controlling module is adapted to receive the status information from the detecting module, and transmit the status information to the code transforming module and/or the storage module.

The storage module is adapted to store the status information detected by the detecting module; and/or the barcodes generated by the code transforming module; and/or additional information such as user status information, device information, measure project identification, management information, etc.

The timing module is controlled by the controlling module, adapted to record the working time of the medical device. The time information output by the timing module may be transmitted to the controlling module, and then be transmitted to the code transforming module by the controlling module to be transformed to the barcodes with other status information detected during the period recorded in the time information.

The statistical analysis module is also controlled by the controlling module, and is adapted to receive the status information from the controlling module for statistical analysis. The analyzed status information may be transmitted to the code transforming module to be transformed to the barcodes, which will be finally transmitted to a hospital or medical institution by the code transforming module. In an embodiment, the analyzed status information may also be transmitted to the controlling module directly, and be outputted and displayed for a user via the output module.

Those skilled in the art can understand that, although the controlling module shown in FIG. 10 is described as an essential technical feature, in practice, the medical device may not include the controlling module. In this case, the functions of the controlling module may be implemented by other modules.

Figure 11:
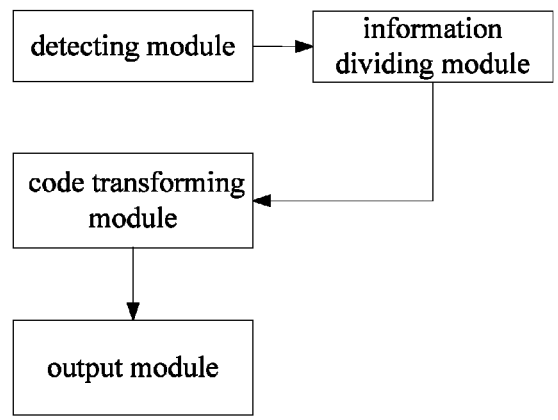
FIG. 11 illustrates the structure diagram of a medical device according to another embodiment of the present invention.

FIG. 11 illustrates the structure diagram of a medical device according to another embodiment of the present invention. As shown in FIG. 11, based on the structure shown in FIG. 9, the medical device further includes an information dividing module, which is adapted to divide the status information to a number of information units, at this situation, the code transforming module is adapted to transform the information units to the barcodes respectively.

Figure 12:
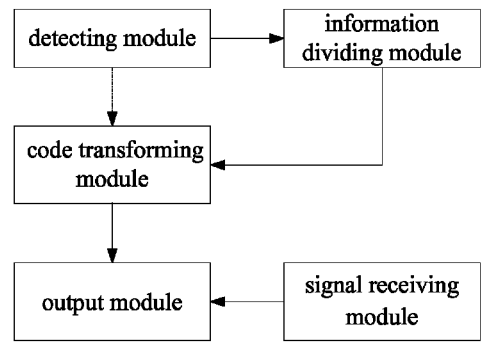
FIG. 12 illustrates the structure diagram of a medical device according to another embodiment of the present invention.

FIG. 12 illustrates the structure diagram of a medical device according to another embodiment of the present invention. As shown in FIG. 12, based on the structures shown in FIG. 9 or FIG. 10, the medical device further includes: a signal receiving module, which is adapted to receive a trigger signal indicating the current barcode or current group of the barcodes has been read. A next group of barcodes will be triggered to be displayed according to the trigger signal. According to an embodiment of the present invention, the signal receiving module may be an optical sensor or a sound sensor. In an embodiment, the signal receiving module may also be a device carrying electrical signal.

It should be noticed that, any combination of the above modules may be integrated as a composite module with multiple functions, which may be considered as a combination of multiple functional modules. Meantime, any combinations of the described modules and the prior art, as long as the combination can be implemented, should be considered within the protection scope of the present invention.

Figure 13:
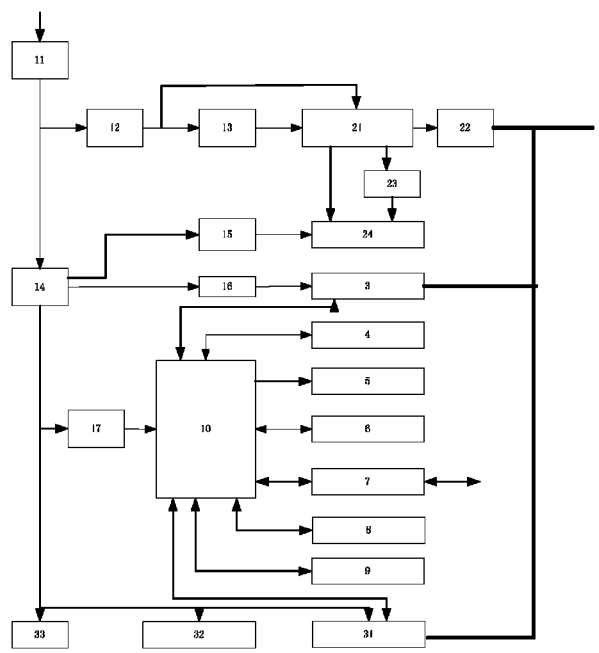
FIG. 13 illustrates the structure diagram of a medical ventilator according to an embodiment of the present invention.

FIG. 13 is the structure diagram of a medical ventilator according to an embodiment of the present invention. As shown in FIG. 13, the a medical ventilator includes: an electrical power system, a motor system, a flow sensor 3, a moisture sensor 4, a display module 5, a SD card 6, a UART 7, a trigger information receiving module 8, a key button 9, a processor 10 and a pressure and snore detecting system.

Herein, the electrical power system includes a voltage convertor 11, adapted to convert external voltage to 24V direct voltage; an current filter 12; a voltage convertor 13, adapted to convert the voltage output by the current filter 12 to 15V, for the power supply of a drive circuit of the motor system; a voltage convertor 14, adapted to convert the voltage output by the voltage convertor 11 to 5V direct voltage, which could supply power for a buzzer and pressure acquisition. The 5V voltage is also the input of voltage convertors 15, 16 and 17. The voltage convertors 15, 16 and 17 convert the 5V voltage to 3.3 V to supply power for a controlling circuit of the motor system, the flow sensor, the processor and peripheral circuits. The motor system includes the controlling circuit 24, the drive circuit 21, a current and back emf drive module 23 and a motor 22. The pressure and snore detecting system includes a pressure and snore detecting module 31, an amplification module 32 and a buzzer 33. The pressure and snore detecting module 31 and the flow sensor 3 are adapted to detect the flow rate and the pressure output by the motor respectively, so that the air pressure and flow supplied to a patient can be controlled. The pressure and snore detecting module 31 is also adapted to detect a snore signal. The UART 7, as an input/output interface to communicate with a PC, is adapted to transmit data to PC for playback purpose and implement software update. The SD card 6 is adapted to store the information, and the information stored in SD card 6 is read and written by the processor 10, and alternatively via SPI bus. The information stored in the SD card 6 may be transmitted to PCs via the UART 7 or a card reader. The trigger information receiving module 8, which may be a light/sound sensor, is adapted to inspect a trigger signal generated when barcodes displayed by the display module 5 are successfully read by the reading device. According to an embodiment of the present invention, the information transmitting may be implemented by software. The software may be installed in the processor 10 via the UART 7. Through the pressure and snore detecting module 31, the flow sensor 3 and the moisture sensor 4, the processor 10 collects therapy information when the medical ventilator is working; and further displays the barcodes corresponding to the therapy information collected on the display module 5, and updates the display according to a trigger signal detected by the light/sound sensor 8. A user could also choose to use the key button 9 to control the display of the barcodes on the display module 5. In an embodiment, the generated barcodes may also be stored in the SD card 6. Those skilled in the art can understand that, the SD card 6 is not an essential feature of the present invention; meantime, the type of the electrical power system may varies according to types of the motor system, the flow sensor 3, the processor 10 and the buzzer 33.

Figure 14:
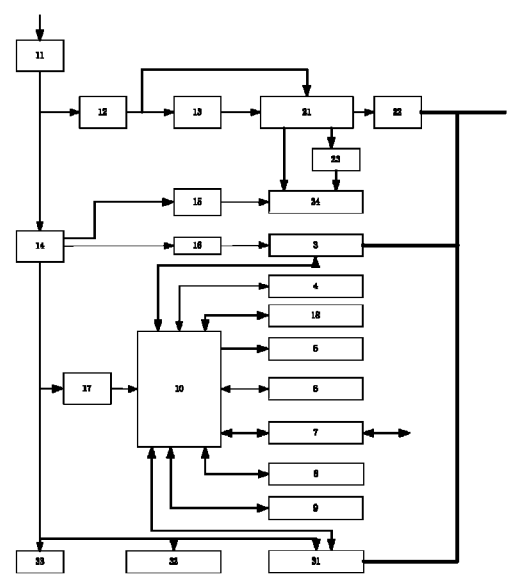
FIG. 14 illustrates the structure diagram of a medical ventilator according to another embodiment of the present invention.

FIG. 14 illustrates the structure diagram of a medical ventilator according to another embodiment of the present invention. As shown in FIG. 14, compared with the medical ventilator shown in FIG. 13, the ventilator further includes a barcode generating module 18 connecting with the processor 10 and the display module 5. The barcode generating module 18, as a hardware chip/module, is adapted to generate barcodes according to the input information in a specific format and communicate with the processor 10 via a specific interface. In this case, in order to achieve the purpose of the present invention, the processor 10 is mainly adapted to collect the therapy information when the medical ventilator is working, via the pressure and snore sensor 31, the flow sensor 3 and the moisture sensor 4; and output the therapy information to the barcode generating module 18 in a specific format. Then the barcodes are generated by the barcode generating module 18 according to the format of the input information. Under the control of the processor 10, the barcodes are displayed on the display module 5 (the display is automatically updated via the optical/sound sensor 8 or manually operated via the key buttons 9).

According to an embodiment of the present invention, the medical ventilator may only include the barcode generating module 18, but without the trigger information receiving module 8. In an embodiment, those skilled in the art can understand that, due to the variety of the medical ventilator, one or more components shown in FIG. 13 and FIG. 14 could be deleted, or, the medical ventilator may further include one or more components. All combinations should be considered as within the protective scope of the present invention.

Figure 15:
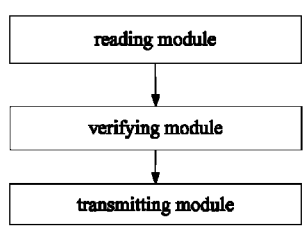
FIG. 15 illustrates the structure diagram of a data reading device according to an embodiment of the present invention.

FIG. 15 illustrates the structure of a data reading device according to an embodiment of the present invention. The data reading device may be the same hardware device as a scanner in the embodiments above. As shown in FIG. 15, the data reading device includes: a reading module, adapted to read a barcode output by a medical device. According to an embodiment of the present invention, the reading module may include a scanner, or may be a hardware device with barcode scanning software. Since the barcode is read at the side of a user of the medical device, to facility the reading for the user, the reading module may be a photograph device, such as a cell phone, a laptop, a pad and another device with a photograph function. According to an embodiment of the present invention, trigger information is generated after a successful barcode reading, collected and detected by an information receiving module of the medical device. The update of the display or the display of a next barcode page could be triggered after the reception of the trigger information by the trigger information receiving module of the medical device.

In some embodiments, the reading module could be divided into a reception sub-module and a parsing sub-module. Herein, the reception sub-module is adapted to receive barcodes output by the medical device while the parsing sub-module is adapted to parse the barcodes to get information which could be analyzed and understood by medical personnel and/or medical devices. According to an embodiment of the present invention, the data reading device further includes a report generating module, adapted to generate a report based on the information output from the parsing sub-module. According to an embodiment of the present invention, there may be a parsing module separated with the reading module.

According to an embodiment of the present invention, a verification module may be further included, adapted to verify whether device identity matches user identity when the barcode includes the information of the device identity and user identity. If the verification module confirms the match, the parsing module parses the barcodes; otherwise, a reject message is sent and no parsing is implemented. The reject message may be an alarm signal. Moreover, the verification module may further send the reject message to a cell phone, a PC or other terminals of a patient and/or medical personnel. By using the technical scheme, errors, occurring during the process of analyzing the status information of several users, can be avoided.

According to an embodiment of the present invention, the reading module may further transform the barcodes to a transmittable file.

In this case, the data reading device described in this embodiment may further includes a transmitting module, adapted to transmit the transmittable file. Since the transmittable file are required to be transmitted to remote terminals or servers, the transmitting module may be a device supporting network communication (internet or 3G network), such as a PC supporting network communication or a cell phone, etc.

According to an embodiment of the present invention, the reading module and the transmitting module may be integrated as an integrated device. The integrated device may be a cell phone with a camera or a PC with a camera and supporting network communication. In this case, none of external devices and no extra cost are necessary during the reading and analyzing process, only software having related functions is installed on the cell phone or PC, so that the cost is reduced and the facility experience is improved.

As described in the above embodiments, the parsing sub-module may also be provided as an independent system, which may be software available in a terminal and installed by a patient or doctor on their PCs or handheld device so that the barcodes could be decoded and the plaintext could be showed. The parsing sub-module may also be a web service. The patient or doctor may input string code acquired into the website, the website returns the patient and doctor the plaintext of barcodes after analyzed.

Those skilled in the art can understand that, to facilitate the comprehension, the embodiments are described in an order of system, method and device. However, all of the embodiments described above may be combined with each other and are not limited by the logical relationship.

According to an embodiment of the present invention, storage medium storing software achieving a method of tele-transmitting information of a medical device is provided. The purpose of the present invention could be achieved by running the software on a device, which has a processor and is able to communicate with current information detecting system and a display module of the medical device.

According to an embodiment of the present invention, a storage medium storing software that performs a data reading method as described is provided. By running the software stored on a device having barcode scanning function (or with camera and barcode recognition function), the purpose of the present invention also can be achieved.

The PCT document is originally filed and published in Chinese, while being translated for national stage, due to the differences between Chinese and the target language, there may be little difference in words between the PCT publication and the national stage specification; however, those do not affect the protection scope of the present invention. For example, when the document is translated from Chinese to English, any meaning differences, caused by specifying or not specifying, singular or plural form, should be considered to be within the protection scope of the present invention.

The above contents are the descriptions of the preferred embodiments of the present invention, which cannot be used to limit the protection scope of the present invention. Under the principle and the novel feature of the present invention, any modifying, equivalent replacement, improvement, etc. are all considered to be within the protection scope of the present invention.

The invention claimed is:

1. A method of tele-transmitting information of a medical device, comprising:
    collecting and detecting therapy and/or status information of the medical device;
    transforming the therapy and/or status information of the medical device to one or more barcodes;
    outputting the one or more barcodes via an output device of the medical device,
    wherein transforming the therapy and/or status information of the medical device to one or more barcodes comprises:
    transforming the therapy and/or status information of the medical device to a string code in accordance with a predefined rule, and taking the string codes as the one or more barcodes directly or transforming the string code to a two-dimensional code and taking the two-dimensional code as the one or more barcodes,
    wherein the barcodes further comprises the serial number of the medical device; by using the serial number of the medical device, the string code would be verified.

2. The method of claim 1, further comprising:
    dividing the collected and detected therapy and/or status information to more than two information units;
    wherein, transforming the therapy and/or status information of the medical device to one or more barcodes comprises:
    transforming the more than two information units to one or more barcodes.

3. The method of claim 2, wherein, when transforming the more than two information units to one or more barcodes, the barcode further comprises one or more controlling data comprising data identification, location identification, totality identification, and time identification.

4. The method of claim 1, wherein, outputting the barcodes via an output device of the medical device comprises:
    displaying the barcodes in groups;
    and the method further comprises:
    receiving a trigger signal, wherein the trigger signal is generated during or after the displayed barcodes being read;
    triggering to display a next group of barcodes according to the tripper signal.

5. The method of claim 4, wherein, the trigger signal is an optical and/or sound signal automatically generated during the barcodes are shot/scanned.

6. The method of claim 1, wherein, the barcodes includes any one or any combination of ASCII code, one-dimensional code, two-dimensional code, three-dimensional code, complex code and character string.

7. The method of claim 1, wherein, transforming the therapy and/or status information of the medical device to barcodes comprises:
    transforming the therapy and/or status information to a data frame firstly, and then transforming the data frame to the barcodes.

8. The method of claim 1, wherein, before transforming the string code to a two-dimensional code, the method further comprises:
    decoding the string code in accordance with the opponent rule; determining whether the information decoded from the string code matches the original information; transforming the string code to the two-dimensional code if matches.

9. The method of claim 1, further comprising: a user interface, providing all kinds of therapy and/or status information which could be detected by the medical device to be selected by a user;
    wherein, collecting and detecting therapy and/or status information of the medical device comprises:
    collecting the therapy and/or status information selected by the user.

10. The method of claim 1, wherein, outputting the one or more barcodes via an output device of the medical device comprises:
    printing the one or more barcodes on papers if the output device of the medical device is a small printer port; or
    displaying the one or more barcodes on a display screen if the output device of the medical device is the display screen; or
    outputting the one or more barcodes to an external storage if the output device of the medical device is a kind of electron port.

11. The method of claim 1, wherein, the status information comprises any or any combination of: the number of treatment day, average daily treatment time, treatment pressure, respiratory disturbance index, snoring index, air leakage, identity information of the medical device, identity information of a user.

12. A method of data reading comprising:

reading one or more barcodes output by a medical device;

parsing the one or more barcodes to obtain therapy and/or status information;

generating a report according to the therapy and/or status information obtained, wherein before or after parsing the one or more barcodes to obtain therapy and/or status information, the method further comprises verifying the one or more barcodes, wherein the one or more barcodes are generated by:

transforming the therapy and/or status information to a string codes in accordance with a predefined rule, and taking the string codes as the one or more barcodes directly or transforming the string code to a two-dimensional code and taking the two-dimensional code as the one or more barcodes;

wherein verifying the one or more barcodes comprises:

verifying whether the length of the string code is right and characters contained are legal, wherein the method further comprises acquiring the serial number of the medical device, wherein verifying the one or more barcodes further comprises verifying whether the string code matches the serial number of the medical device.

13. The method of claim 12, wherein, the one or more barcodes are generated by: transforming the therapy and/or status information to a data frame firstly, then transforming the data frame to the one or more barcodes;

wherein, verifying the one or more barcodes comprises:

parsing the one or more barcodes to acquire the data frame, and verifying information body of the data frame according to the check code of the data frame.

14. The method of claim 12, wherein, parsing the one or more barcodes to obtain therapy and/or status information and generating a report according to the therapy and/or status information obtained comprises:

transmitting the one or more barcodes to a server, parsing the one or more barcodes after a successful verification of the barcode by the server;

generating a report according to the therapy and/or status information obtained from paring the one or more barcodes.

* * * * *